United States Patent [19]

Tam et al.

[11] Patent Number: 4,837,311
[45] Date of Patent: Jun. 6, 1989

[54] ANTI-RETROVIRAL COMPOUNDS

[75] Inventors: Steve Tam, West Caldwell; Manfred Weigele, North Caldwell, both of N.J.; Samuel Broder, Bethesda; Hiroaki Mitsuya, Rockville, both of Md.

[73] Assignees: Hoffman-La Roche Inc., Nutley, N.J.; United States of America, Washington, D.C.

[21] Appl. No.: 64,631

[22] Filed: Jun. 22, 1987

[51] Int. Cl.$^4$ .................. A61K 31/70; A61K 9/00; A61K 9/22

[52] U.S. Cl. ................................ 536/22; 536/23; 536/24; 536/26; 536/27; 536/28; 536/29; 514/44; 514/46; 514/47; 514/48; 514/49; 514/50; 514/51

[58] Field of Search ................ 514/43, 44, 46, 47, 514/48, 49, 50, 51; 536/22, 23, 24, 26, 27, 28, 29

[56] References Cited

U.S. PATENT DOCUMENTS 4,724,232  2/1988  Rideout et al. .................. 514/50

OTHER PUBLICATIONS

Broder; AIDS, Modern Concepts and Therapeutic Challenges; 303-333, 1987, Marcel Dekker, Inc. New York.

Mitsuya and Broder, Strategies for Antiviral Therapy in AIDS, Nature vol. 325, No. 6017, Feb. 87, 773-778.

Yarchoan and Broder, Special Report: Development of Anti-Retroviral Therapy for the Acquired Immunodeficiency Syndrome and Related Disorder, New England Journal of Medicine vol. 316, Feb. 26, 87, 557-564.

Dahlberg, et al., Broad Spectrum Anti-Retroviral Activity of 2',3'-dideoxynucleosides, Proceedings of the National Academy of Sciences U.S.A., vol. 84 (1987) 1-5.

Mitsuya et al., 3'-Azido-3'Deoxythymidine: An Antiviral Agent that Inhibits the Infectivity and Cytopathic Effect of Human T-Lymphotropic Virus Type III/-Lymphadenopathay—Associated Virus in Vitro. Porceedings of the National Academy of Sciences U.S.A., vol. 82, Oct. 1985, 7096-7100.

Wapar et al., Effects of 2,',3'-Dideoxynucleosides on Mammalian Cells and Viruses, Journal of Cellular Physiology 121: 402-408 (1984).

Great Britain Application No. 8512330, published May 15, 1985.

Great Britain Patent No. 2 181 128 A published Apr. 15, 1987.

Europen Patent Application No. 86307071.0 published Apr. 8, 1987.

Australian Patent Application No. AU-A-54758/86 published Mar. 12, 1986.

Australian Patent Application No. AU-A-54757/86 published Mar. 14, 1986.

*Primary Examiner*—John Kight
*Assistant Examiner*—Nathan M. Nutter
*Attorney, Agent, or Firm*—Jon S. Saxe; George M. Gould; Julie M. Prlina

[57] ABSTRACT

A-B-C wherein A and C are each independently 2',3' dideoxynucleosides and B is a linking group; and a method of treating or preventing a retroviral injection in a subject by administering the compounds of the invention.

41 Claims, 1 Drawing Sheet

ANTI-RETROVIRAL COMPOUNDS

BACKGROUND OF THE INVENTION

The field of viral chemotherapeutics has recently developed in response to the particularly challenging problems presented with respect to the diagnosis and treatment of viral diseases. Of particular interest is the development of compounds effective against retroviruses, most particularly the HIV virus.

The effectiveness of any antiviral chemotherapeutic naturally depends on many factors including the identification of the specific virus, an understanding of its infectivity, life cycle, replication, and spread within the infected host.

All viruses must replicate and transcribe their nucleic acids into messenger RNA which in turn translates into proteins for progeny virions. For DNA viruses, the virus synthesizes its own DNA polymerase enzyme which uses the cell's supply of purines and pyrimidines to make additional copies of the viral DNA.

Retroviruses are characterized in that they are able to synthesize DNA from the RNA template which comprises their genetic material via a polymerase enzyme "reverse transcriptase" and are therefore characterized as retroviruses. This DNA, which corresponds to the RNA version of the viral genome, is then incorporated into the host cell genome viral DNA is synthesized in the course of the normal host cell processes. The HIV virus is characteristically a retrovirus and possesses the enzyme reverse transcriptase.

Antiviral compounds with various modes of action are known in the art. For example, a class of compounds known as nucleoside analogs exhibit broad antiviral activity by interfering with the viral life cycle.

These "fraudulent" nucleosides are analogs of the normal DNA or RNA building blocks; adenosine, thymidine, cytidine, guanosine or uridine, 2'-deoxyadenosine, 2'deoxycytidine and 2'deoxyguanosine. However, unlike their normal counterparts these compounds cannot be used in normal DNA or RNA synthesis. In the cell these fradulent nucleosides deceive the virus into thinking they are normal DNA or RNA building blocks. The "frausulent" counterpart is utilized in the viral life cycle ultimately resulting in viral suicide.

Unfortunately, most of these antiviral substances are not specific inhibitors of only viral processes. Most of these compounds will interfere to a greater or lesser degree with normal molecular processes of the host cell resulting in toxic effects on uninfected cells. Thus, in viral chemotherapeutics the quest is for an antiviral drug which interferes with only virus coded processes and not the normal molecular processes of uninfected mammalian cells.

SUMMARY OF THE INVENTION

The instant invention comprises compounds which exhibit antiretroviral activity. These compounds act to interfere with the viral life cycle, but do not exhibit the extreme toxic effects on the normal cellular processes of mammalian host cells.

The instant invention also comprises all the novel intermediate compounds used in the synthesis of the compounds of the invention.

The instant invention also comprises a method of preventing a retroviral infection in a subject or treating a subject infected with a retrovirus by administering to the subject a virus inactivating effective amount of the compounds of the invention or the pharmaceutically acceptable salts.

Particularly preferred is a method of preventing an HIV infection in a subject or treating a subject infected with the HIV virus by administering to the subject a virus inactivating effective amount of the compounds of the invention or the pharmaceutically acceptable salts.

The compounds of the instant invention are represented by the general formula

A—B—C wherein A and C are each independently dideoxynucleoside radicals; and B is a linking group represented by the formula

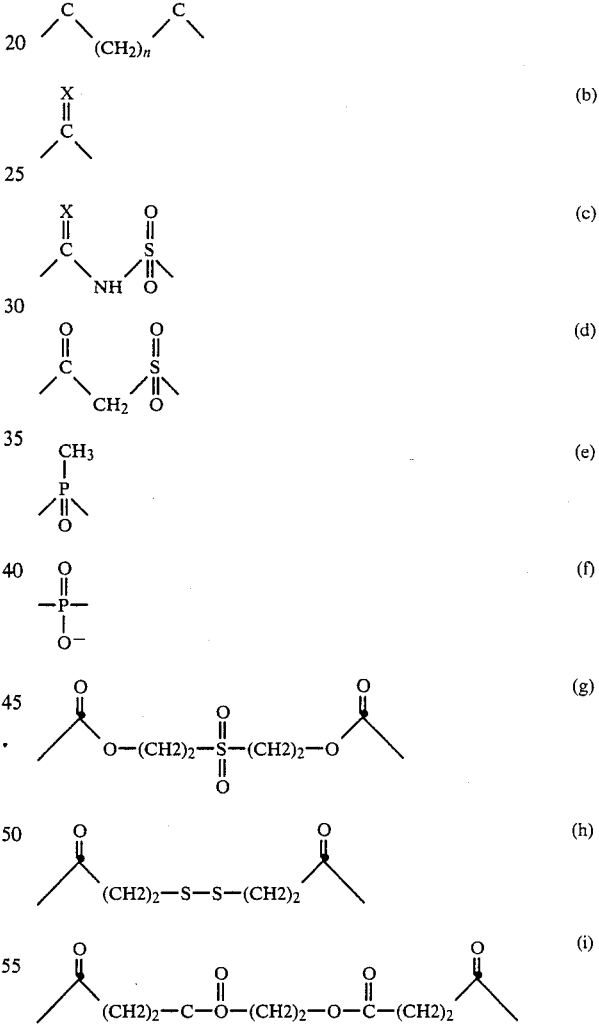

with X=O or S and n=2-6; and B is attache to A at either the 5' hydroxy position or the amino position of A; and C is attached to B at either the 5' hydroxy position or the amino position of C; or the pharmaceutically acceptable salts.

The term dideoxynucleoside radical means any 2', 3' dideoxy analog of adenosine, thymidine, cytidine, guanosine, uridine or inosine wherein two hydroxy substituents are absent from the 2' and 3' positions on the ribose portion of the nucleoside molecule.

Particularly included are substituted 2'-3' dideoxynucleoside radicals of the above general formula where the substituents are those such as amino, halogen, alkyl, azido, cyano, and others commonly found on nucleoside analogs.

The invention also comprises all the novel intermediate compounds used to synthesize the compounds of the invention. These novel intermediates include compounds represented by the letter designations A or C as defined in Formula I, which are reacted with conventional hydroxyl or amine blocking groups known in the art. (Such as tertbutyldimethyl chlorosilyl "SiO", or dimethyaminomethylene.

The intermediates also include compounds represented by the letter designations A or C as defined in Formula I, to which the linking group represented by the letter designation B, has been attached.

The intermediates also include compounds represented by the letter designation A or C as defined in Formula I, to which the linking group represented by the letter designation B has been attached, and where one or more of the remaining 5' hydroxy positions or the amino positions is blocked by a conventional hydroxyl or amine blocking group known in the art.

The intermediates also include compounds of the formula A—B—C wherein A, B and C are as defined in Formula and one or more of the 5' hydroxy positions or amino positions of A or C which is not linked to B is blocked by a conventional hydroxyl or amine blocking group known in the art.

The invention also comprises a method of preventing a retroviral infection in a subject or treating a subject infected with a retrovirus by administering a virus inactivating effective amount of the Formula I compounds or their pharmaceutically acceptable salts.

Particularly preferred is a method of preventing an HIV infection in a subject or treating a subject infected with the HIV virus by administering a virus inactivating effective amount of the Formula I compounds or their pharmaceutically acceptable salts.

The instant compounds exhibit antiviral activity without exerting the extreme toxic effects against molecular cellular processes of normal mammalian host cells.

DETAILED DESCRIPTION OF THE INVENTION

The compounds of the instant invention are represented by the general formula

I. A—B—C wherein A and C are each independently dideoxynucleoside radicals; and B is a linking group represented by the formula

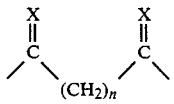 (a)

 (b)

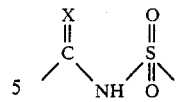 (c)

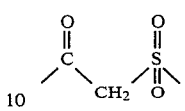 (d)

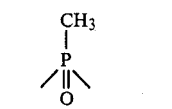 (e)

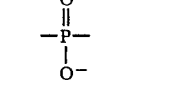 (f)

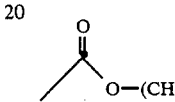 (g)

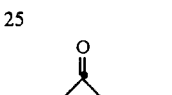 (h)

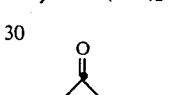 (i)

with X=O or S and n=2-6; and B is attached to A at either the 5' hydroxy position or the 4 amino position of A; and C is attached to B at either the 5' hydroxy position or the amino position of C; or the pharmaceutically acceptable salts.

The term dideoxynucleoside radical means any 2', 3' dideoxy analog of adenosine, thymidine, cytidine, guanosine, uridine or inosine wherein two hydroxy substituents are absent from the 2' and 3' positions on the ribose portion of the nucleoside molecule. Particularly included are substituted deoxynucleoside radicals of the above general formula where the substituents are those such as amino, halogen, alkyl, azido, cyano, and others commonly found on nucleoside analogs.

There are four preferred embodiments represented by the compounds of Formula I, further designated. I(a), I(b), I(c), and I(d).

The first preferred embodiment is a compound of the formula

I(a) A—B—C wherein, A, B, and C are as in Formula I and B is attached to A at the amino position of A, and C is attached to B at the 5' hydroxy position of C.

A preferred embodiment of Formula I(a) is where A or C is selected from the group consisting of dideoxycytidine, dideoxyadenosine, or 3'-azido-3'-deoxythymidine.

A further preferred embodiment of Formula I(a) is where A is dideoxycytidine.

Particularly preferred is a compound of Formula I(a) wherein B is

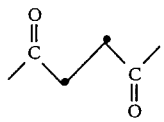

and C is 3'-azido-3'-deoxythymidine said compound having the formula

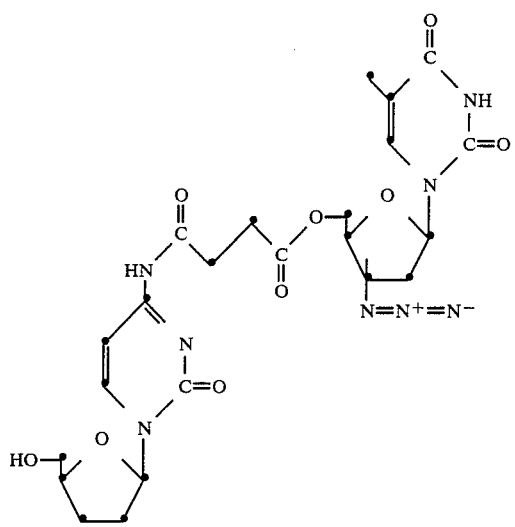

Particularly preferred is a compound of Formula I(a) wherein B is

and C is dideoxycytidine said compound having the formula

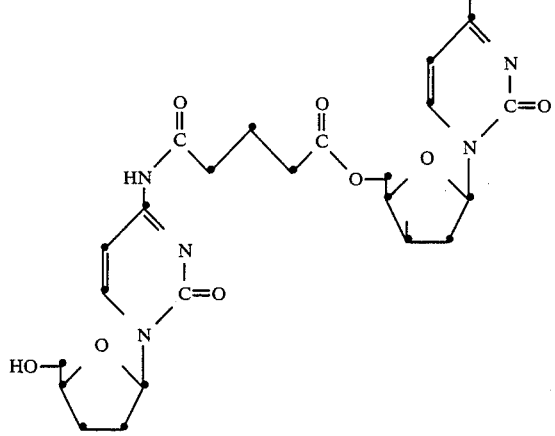

Particularly preferred is a compound of Formula I(a) wherein B is

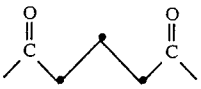

and C is dideoxyadenosine said compound having the formula

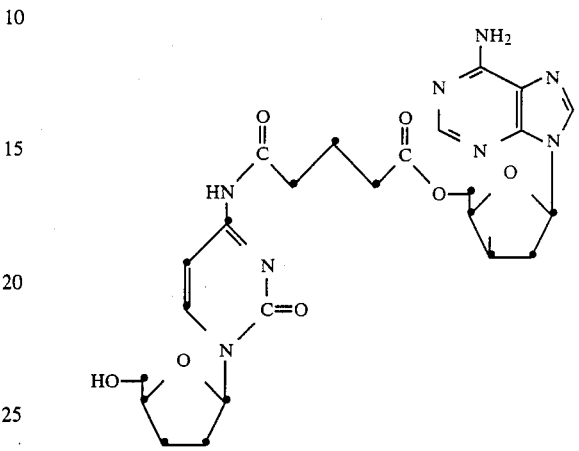

The second preferred embodiment is a compound of the formula

I(b)  A—B—C wherein A, B and C are as in Formula I and B is attached to A at the 5' hydroxy position of A, and C is attached to B at the 5' hydroxy position of C.

A preferred embodiment of Formula I(b) is where A or C is selected from the group consisting of dideoxycytidine, dideoxyadenosine, or 3'-azido-3'-deoxythymidine.

A further preferred embodiment of Formula I(b) is where A is dideoxycytidine.

Particularly preferred is a compound of Formula I(b) wherein B is

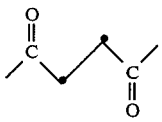

and C is 3'-azido-3'-deoxythymidine said compound having the formula

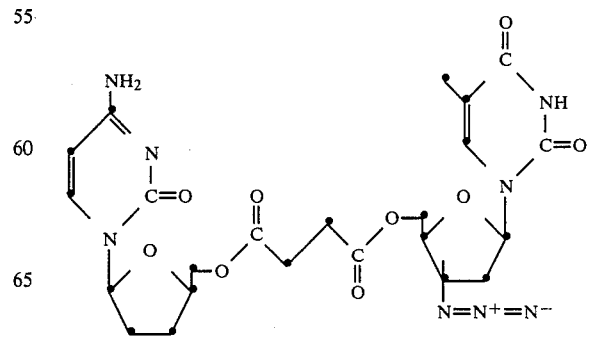

Particularly preferred is a compound of Formula I(b) waherein B is

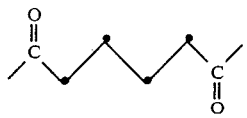

and C is dideoxycytidine said compound having the formula

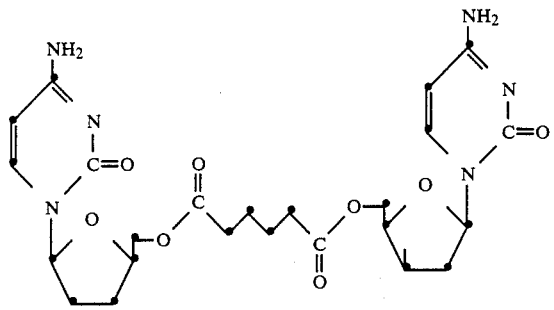

Particularly preferred is a compound of Formula I(b) wherein B is

and C is dideoxycytidine said compound having the formula

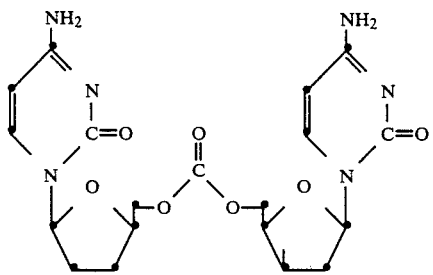

The third preferred embodiment is a compound of the formula

I(c) A—B—C wherein A, B and C are as in Formula I and B is attached to A at the 4 amino position of A and C is attached to B at the 4 amino position of C.

A preferred embodiment of Formula I(c) is where A or C is selected from the group consisting of dideoxycytidine, dideoxyadenosine, or 3'-azido-3'-deoxythymidine.

A further preferred embodiment of Formula I(c) is where A is dideoxycytidine.

Particularly preferred is a compound of Formula I(c) wherein B is

and C is dideoxycytidine said compound having the formula

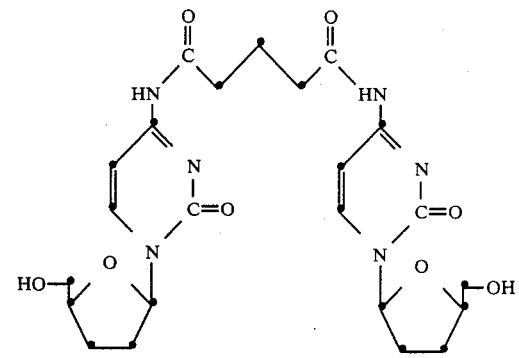

The fourth preferred embodiment is a compound of the formula

I(d) A—B—C wherein A, B and C are as in Formula I and B is attached to A at the 5' hydroxy position of A and B is attached to C at the amino position of C.

A preferred embodiment of Formula I(d) is where A or C is selected from the group consisting of dideoxycytidine, dideoxy adenosine, or 3'-azido-3'deoxythymidine.

A further preferred embodiment of Formula I(d) is where A is dideoxycytidine.

The compounds of Formula I(a), (b), (c) and (d) exhibit antiviral activity without exhibiting extreme toxic effects against normal molecular processes of mammalian host cells.

The instant invention also comprises all the novel intermediates used in the synthesis of the compounds of Formula I. These novel intermediates are made by beginning with compounds represented by the letter deasignations A and C; which are reacted with conventional hydroxyl or amine blocking groups known in the art (such as tertbutyldimethylchlorosilyl or dimethylaminomethylene)

The intermediates also include compounds represented by the letter designations A or C as defined in Formula I, to which the linking group represented by the letter designation B, has been attached.

The intermediates also include compounds represented by the letter designation A or C as defined in Formula I, to which the linking group represented by the letter designation B has been attached, and where one or more of the remaining 5' hydroxy positions or the amino positions is blocked by a conventional hydroxyl or amine blocking group known in the art.

The intermediates also include compounds of the formula A—B—C wherein A, B and C are as defined in Formula I and one or more of the 5' hydroxy positions or amino positions of A or C which is not linked to B is blocked by a conventional hydroxyl or amine blocking group known in the art.

The novel intermediate compounds may be represented by several different formulas.

First, are compounds represented by the letter designation A or C wherein A or C each independently are dideoxynucleoside radicals and the 5' hydroxy position of A or C is blocked with a conventional blocking group known in the art (such as tertbutyldimethylchlorosilane)

A preferred version of these compounds is where A or C each independently is dideoxycytidine and the 5' hydroxy group is blocked with tertbutyldimethylchlorosilane said compound having the formula

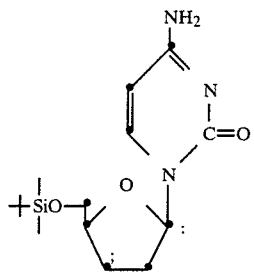

Next are compounds represented by the formula A—B or B—C wherein A or C are each independently dideoxynucleoside radicals and B is a linking group represented by the formula

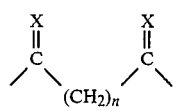 (a)

 (b)

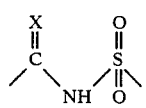 (c)

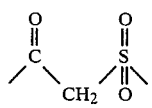 (d)

 (e)

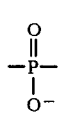 (f)

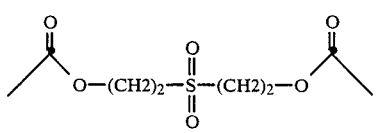 (g)

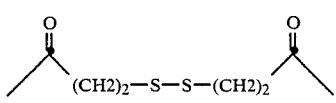 (h)

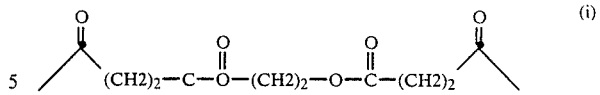 (i)

with X=O, or S and n=2-6 and B is attached to A or C at either the 5' hydroxy position or the amino position of A or C.

Particularly preferred is a compound of the formula A—B or B—C wherein A or C each independently is 3'-azido-3'-deoxythymidine and B is

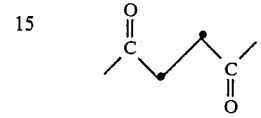

and B is attached to A or C at the 5' hydroxy position of A or C; said compound having the formula

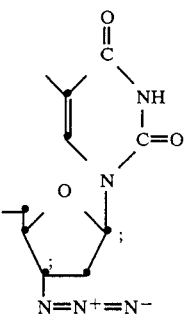

Further novel intermediates included within the present invention are compounds repesented by the formula A—B or B—C wherein A or C are each independently a dideoxynucleoside radical and B is a linking group represented by the formula

 (a)

 (b)

 (c)

 (d)

 (e)

 (f)

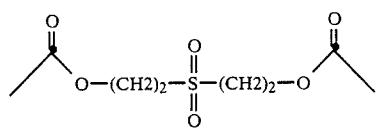 (g)

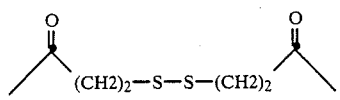 (h)

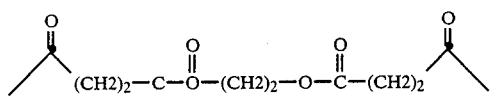 (i)

with X=O, or S and n=2-6 and B is attached to A or C at either the 5' hydroxy position or the amino position of A or C and the remaining amino or hydroxy position of A or C is blocked with a conventional hydoxyl blocking group known in the art.

Particularly preferred are compounds wherein A or C are each independently dideoxycytidine and B is

and B is attached to A at the 4-amino position of A, and the 5' hydroxy position of A is blocked; said compound having the formula

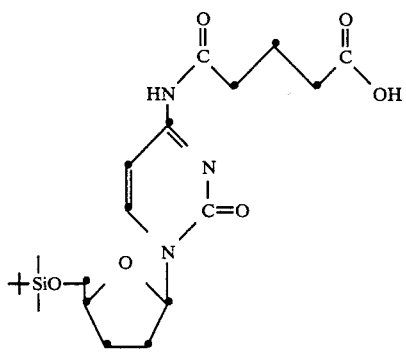

Novel intermediates also included within the present invention are compounds represented by the formula A—B—C wherein A or C are each independently dideoxynucleoside radicals and B is a linking group represented by the formula

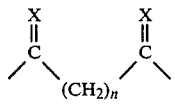 (a)

 (b)

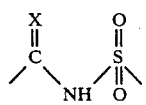 (c)

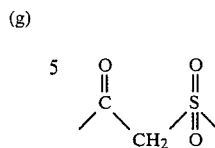 (d)

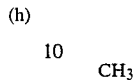 (e)

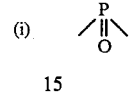 (f)

 (g)

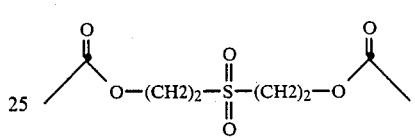 (h)

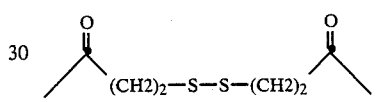 (i)

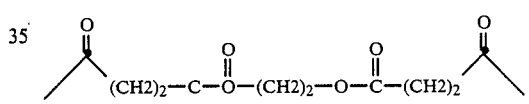

with X=O, or S and n=2-6 and B is attached to A at either the 5' hydroxy position of the amino position of A, and C is attached to B at either the 5' hydroxy position or the amino position of C; and the remaining 5' hydroxy positions of A or C are blocked with a conventional blocking group known in the art (such as tert-butyldimethylchlorosilane).

A particularly preferred version of the above compound is where A is dideoxycytidine, and C is 3'-azido-3'-deoxythymidine and B is

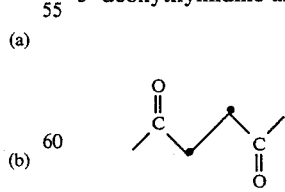

and B is attached to A at the 4 amino position of A and C is attached to B at the 5'hydroxy position of C, and the 5' hydroxy position of A is blocked; said compound having the formula

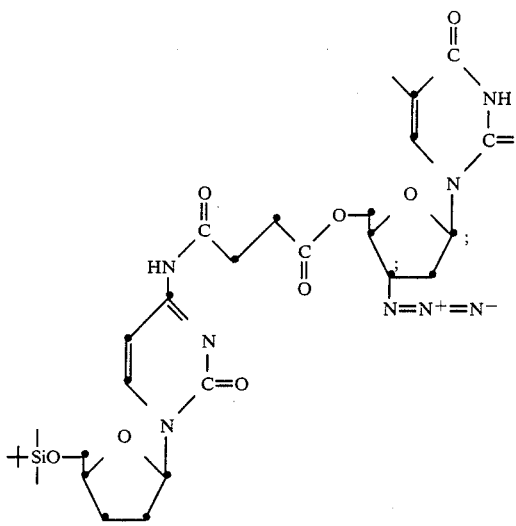

Also particularly preferred is where A and C are dideoxycytidine and B is

and B is attached to A at the 4 amino position of A and C is attached to B at the 4 amino position of C and the 5' hydroxy positions of A and C are blocked; said compound having the formula

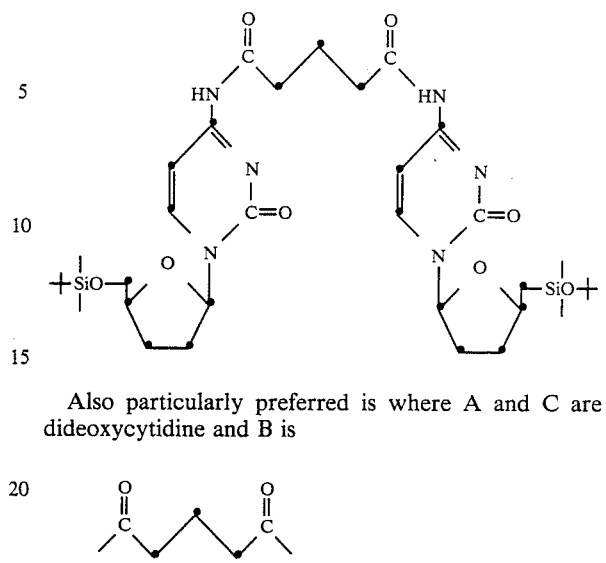

Also particularly preferred is where A and C are dideoxycytidine and B is

and B is attached to A at the 4 amino position of A and C is attached to B at the 5' hydroxy position of C and the 5' hydroxy position of A is blocked; said compound having the formula

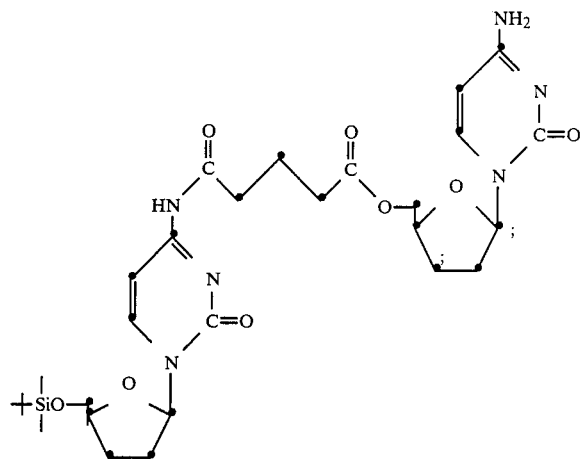

Also particularly preferred is where A is dideoxycytidine and C is dideoxyadenosine and B is

and B is attached to A at the 4 amino position of A and C is attached to B at the 5' hydroxy position of C, and the 5' hydroxy position of A is blocked; said compound having the formula

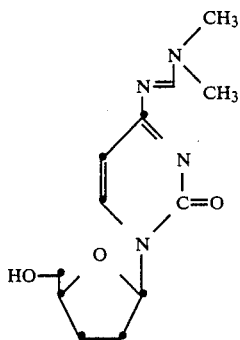

The novel intermediates of the instant invention also include compound represented by the letter designation A or C which are blocked with a conventional amine blocking group known in the art.

Particularly preferred is where A and C are dideoxycytidine and the amine blocking group is dimethylaminomethylene said compound having the formula

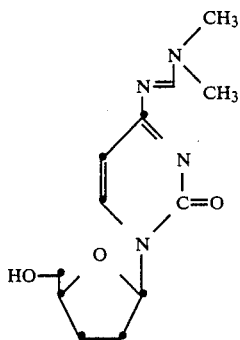

Next are compounds represented by the formula

, A—B—C wherein A B and C are as in formula I and B is attached to A at the 5' hydroxy position of A, and B is attached to C at the 5' hydroxy position of C and the amino positions of A and C are blocked by a conventional amine blocking group known in the art.

Particularly preferred is where A and C are dideoxycytidine and the amine blocking group is dimethylaminomethylene said compound having the formula

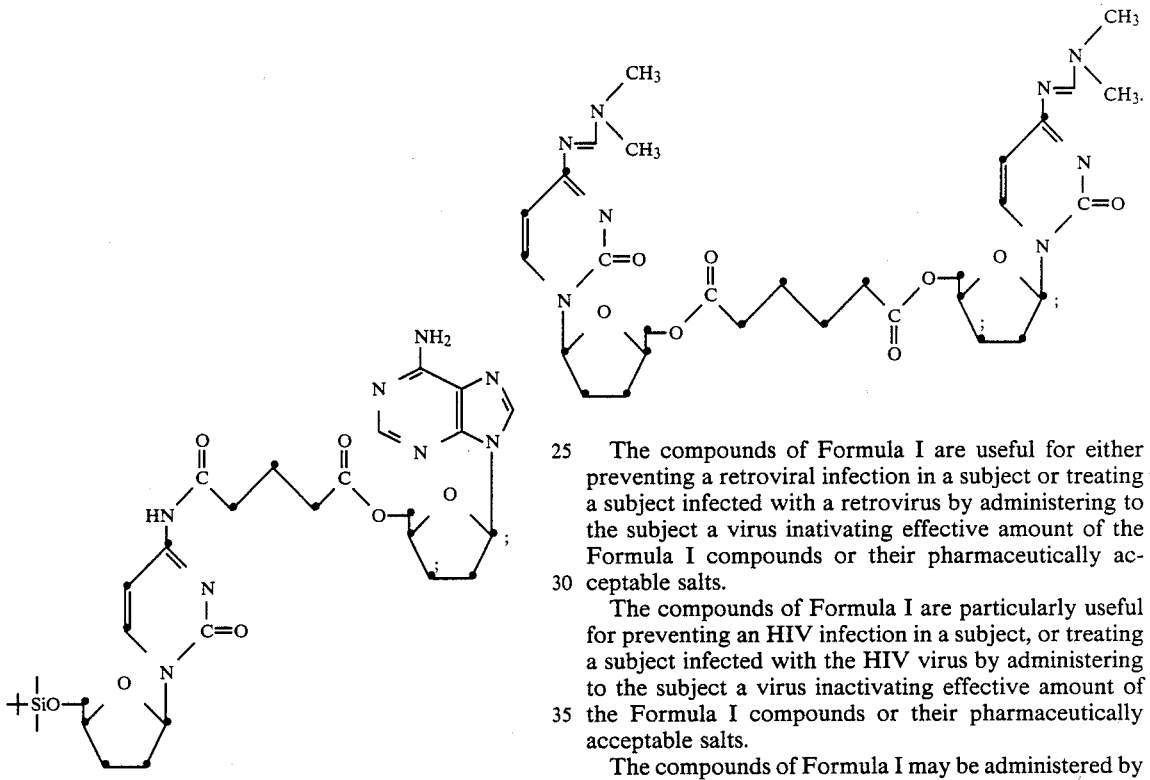

The compounds of Formula I are useful for either preventing a retroviral infection in a subject or treating a subject infected with a retrovirus by administering to the subject a virus inativating effective amount of the Formula I compounds or their pharmaceutically acceptable salts.

The compounds of Formula I are particularly useful for preventing an HIV infection in a subject, or treating a subject infected with the HIV virus by administering to the subject a virus inactivating effective amount of the Formula I compounds or their pharmaceutically acceptable salts.

The compounds of Formula I may be administered by any suitable route including orally and intravenously. Generally a suitable dose of the compounds of Formula I will be in the range of 1–150 mg/kg/day administered over 2–6 subdoses per day.

While it is possible for the Formula I compounds to be administered alone it is preferable to present it as a pharmaceutical formulation. The formulations of the invention comprise at least one compound of Formula I together with one or more acceptable carriers thereof and optionally other therapeutic agents. Each carrier must be "acceptable" in the sense of being compatible with the other ingredients of the formulation and not injurious to the patient. Formulations include those suitable for oral, and intraveneous administration. The formulations may conveniently be presented in unit dosage form and may be prepared by any methods well known in the art of pharmacy.

Formulations of the present invention suitable for oral administration may be presented as discrete units such as capsules, cachets or tablets each containing a predetermined amount of a Formula I compound; as a powder or granules; as a solution or a suspension in an aqueous or non-aqueous liquid; or as an oil-in-water liquid emulsion or a water-in-oil liquid emulsion. The Formula I compound may also be presented as a bolus, electuary or paste.

A tablet may be made by compression or molding, optionally with one or more accessory ingredients. Compressed tablets may be prepared by compressing in a suitable machine the Formula I compound in a free-flowing form such as a powder or granules, optionally mixed with an appropriate binder, lubricant, inert diluent, preservative, distinegrant, surface-active, or dispersing agent. Molded tablets may be made by molded in a suitable machine a mixture of the powdered compound moistened with an inert liquid diluent. The tablets may optionally be coated or scored and may be formulated so as to provide slow or controlled release of the active ingredient therein using for example, hydroxypropylmethyl cellulose in varying proportions to provide the desired release profile.

Formulations suitable for intraveneous administration include aqueous and non-aqueous isotonec, sterile injection solutions which may contain anti-oxidants, buffers, bacteriostats and solutes which render the formulation isotonic with the blood of the intended recipient; an aqueous and non-aqueous sterile suspensions which may include suspending agents and thickening agents. The formulations may be presented in unit-dose or multi-dose sealed containers, for example, ampules or vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets of the kind previously described.

Preferred unit dosage formulations are those containing a daily dose or unit, daily subdose, as herein above recited, or an appropriate fraction thereof, of the compounds of Formula I.

The compounds of Formula I consist of hereto and homodimers. The first step in the synthesis of the heterodimers begins with selective protection of the 5'-OH or the amino group of the 2',3'-dideoxynucleoside radical with conventional amine or hydroxy blocking groups known in the art. The general methods of attaching the blocking groups are well known to one skilled in the art. Examples 1 and 13 of the instant specification illustrate one method of attaching known hydroxyl and amine blocking groups respectively. After attachment of the appropriate blocking groups, the bifunctional linker is attached to yield an intermediate with the linker group incorporated onto the unprotected NH$_2$ or 5'—OH group. A subsequent condensation of this intermediate with a second 2',3'-dideoxynucleoside followed by deprotection then yields the heterodimer. Selective protection of the 5'—OH group can be conveniently achieved by reaction with reagents such as tertbutyldimethylsilyl chloride, triphenylmethyl chloride, benzylchloride or tetrahydropyran. The most convenient method for selective protection of the amino group is a reaction with dimethylformamide dimethylacetal to give the dimethylamino methylene derivative of the amine. The preferred bifunctional linker reagents are the cyclic dicarboxylic acid anhydrides, chlorosulfonylisocyanate, carboxyisothiocyanate, carboxyisocyanate, chlorosulfonylacetyl chloride, methyl phosphonyldichloride etc. The condensation of the COOH group with either an OH or an NH$_2$ group is usually carried out in the presence of reagents such as dicyclohexylcarbodiimide/1-hydroxy benzotriazole, 1,1'-carbonyldiimidazole/potassium tert-butoxide, 2-bromo-1-methylpyridinium iodide/triethylamine, or 1,1-oxalyldiimidazole.

The same technology can be used to prepare the homodimers by using two identical 2',3'-dideoxynucleosides radicals.

On the other hand, the homodimers can be prepared by direct reaction of a dideoxymucleoside radicals with a dicarboxylic acid dihalide or other commonly used derivatives such as bis[2-(succinimidoOxycarbonyloxy)ethyl] sulfone, bis(sulfosuccinimidyl)suberate, disuccinimidyl suberate, dithiobis(succinimidyl propionate) etc.

The present invention will be further described in connection with the following Examples which are set forth for the purpose of illustration only.

EXAMPLE 1

2',3'-Dideoxy-5'0[(1,1-dimethylethyl)dimethylsilyl]cytidine

Figure 1:
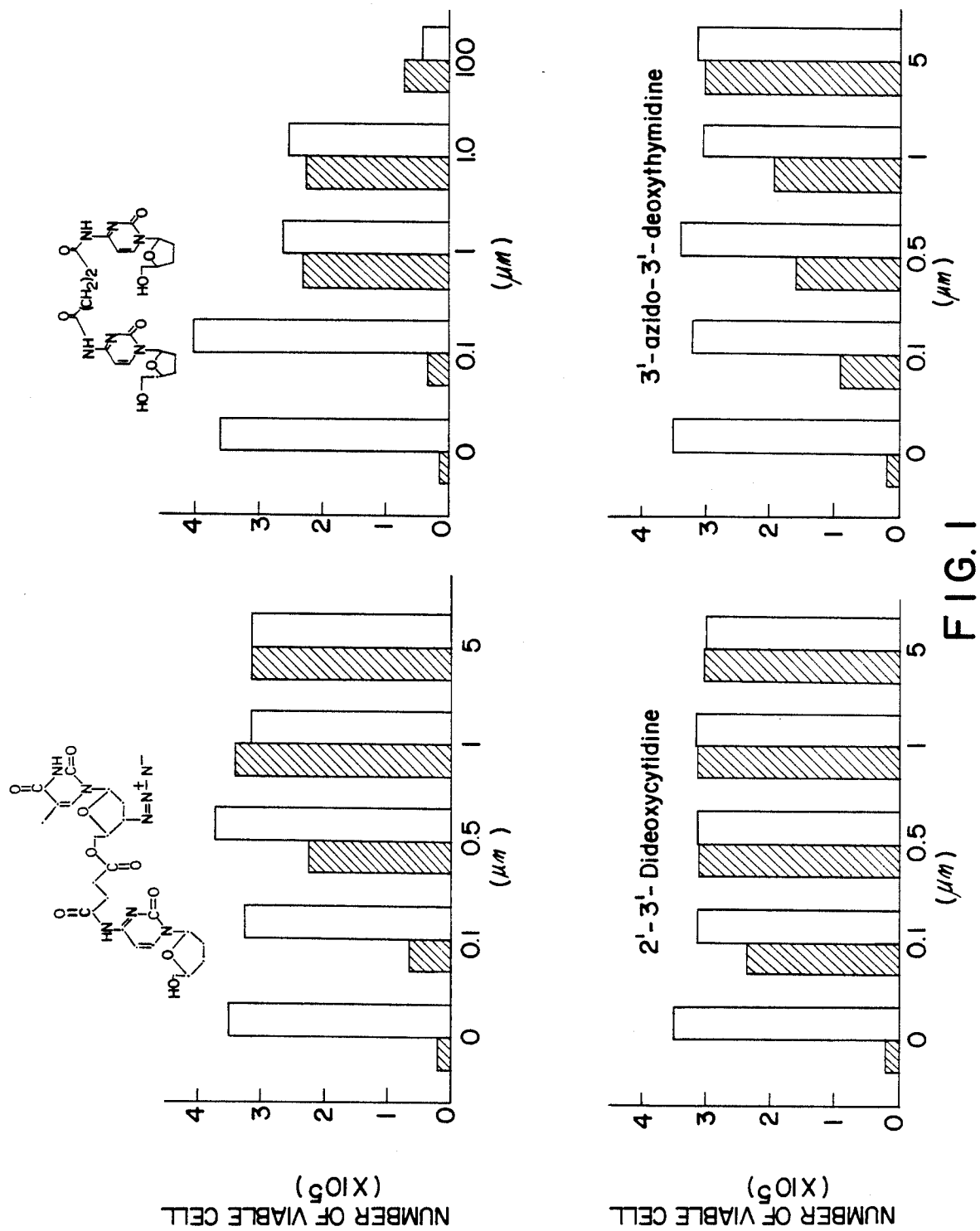
FIG. 1 illustrates the anti-retroviral activity of the instant compounds against HIV. The black bars represent survival of target cells when virus is added. The open bars represent survival in the absence of virus (control). The drug dose is listed along the x-axis.

To a solution of 2.1 g (10 mmol) of 2',3'-dideoxyctyidine in 20 ml of dimethylformamide was added 750 mg (11 mmol) of imidazole and 1.7 g (11 mmol) of tertbutyldimethylchlorosilane. After stirring at ambient temperature for 15 hours, the reaction solution was evaporated in vacuo. The residue was chromatographed (0–10% MeOH in CH$_2$Cl$_2$) to give 5.6 g (75%) of a white solid NMR (CDCl$_3$): 0.1 (s, 6H, 2CH$_3$), 0.9 (s, 9H 3CH$_3$), 1.8–2.7 (m, 4H, H-2's and H-3's), 3.74 (dd, J=2.4 and 11.6 Hz, 1H, H-5'a), 4.09 (dd, J-2.0 and 11.6 Hz, 1H, H-5'b), 4.18 (dt, 1H, H-4'), 5.77 (d, J=8Hz, 1H, H-5), 6.09 (dd, J=2.4 and 6.8 Hz, 1H, H-1'), 8.24 (d, J=8 Hz, 1H, H-6).

EXAMPLE 2

3'-Azido-3'-deoxy-beta-D-erythro-thymidine 5'-(hydrogenbutanedioate)

To a stirred solution of 1.7 g (6 mmol) of 3'-azido-3'-deoxy-beta-D-erythro-thymidine in 20 ml of dimethylformamide was added 198 mg (7.8 mmol) of sodium hydride. After 0.5 hours at ambient temperature. 770 mg (7.7 mmol) of succinic anhydride was added. After another 2 hours, the mixture was applied on a column containing 20 ml of AG 50 (H+) resin and eluted with distilled water. The eluate containing the product was lyophilized to a gummy oil which was purified by silica gel column chromatography (10–25% MeOH in CH$_2$Cl$_2$), to give 2.05 g (93%) of a white solid.

NMR (CDCL$_3$+DMSO-d$_6$): 1.89 (5, 3H, CH$_3$), 2.39 and 2.63 (m, 6H, CH$_2$'s and H-2'), 4.00 (m, 1H, H-3' or H-4', 4.30 (m, 2H, H-3' or H-4' and H-5a), 4.44 (m, 1H, H-5') 6.15 (t, J=7.0 Hz, 1H, H-1'), 7.3 (s, 1H, H-6), 12.4 (bs, 1H, NH), 13.3 (bs, 1H, COOH).

EXAMPLE 3

3'-Azido-3'-deoxy-4[[1-[2',3'-dideoxy-5'-0[(1,1-dimethylethyl)dimethylsilyl]-pentofuranosyl-1,2-dihydro-2-oxopyrimidinyl]amino]beta-D-erythro-thymidine 5'-(4-oxobutanoate) (ester)

To a solution of 210 mg (0.57 mmole) of 3'-Azido-3'-deoxy-beta-D-erythro-thymidine 5'-(hydrogenbutandioate) (from Example 2) in 3 ml of pyridine were added 235 mg (1.14 mmol) of dicyclohexylcarbodiimide and 154 mg (1.14 mmol) of 1-hydroxybenzotriazole. After 2 hours, 186 mg (0.57 mmol) of 2',3'-dideoxy-5'0-[(1,1-dimethylethyl)dimethylsilyl]cytidine (from Example 1) was added and the mixture stirred overnight (16 hours)

at ambient temperature. Water (1.5 ml) was then added to the reaction and the precipitate was removed by filtration and the filtrate was evaporated to dryness in vacuo. The residue was extracted with 50 ml dichloromethane and washed successively with 2×25 ml=50 ml of saturated aqueous sodium bicarbonate and 2×25 ml=50 ml of saturated aqueous sodium chloride and dried over sodium sulfate. Removal of the dichloromethane afforded the crude product as a gummy oil which was purified by silica gel column chromatography (0–10% MeOH in CH$_2$Cl$_2$), to give 270 mg (70%) of a white solid.

NMR (CDCl$_3$): 0.1 (S, 6H, 2 CH$_3$), 0.9 (S, 9H 3 CH$_3$), 1.8–2.9 (m. 13H, H-2's, H-3', 5-CH$_3$ and 2 CH$_2$), 3.5–4.5 (m, 7H, H-3', H-4's), 6.1 (m, 2H, H-1's), 7.3 (m, 2H, H-5 and H-6), 8.58 (d, J=8Hz, 1-H, H-6), 9.04 and 9.8 (2 bs, 2H, 2NH).

EXAMPLE 4

5-N[2'3'-Dideoxy-5'0[(1,1-dimethylethyl)dimethylsilyl]cytidinyl]-5-oxopentaonic acid To a solution of 980 mg (3 mmol) of 2'3'-dideoxy-5'-0[(1,1-dimethylethyl)dimethylsilyl]cytidine (from Example 1) in 6 ml of dimethylformamide was added 420 mg (3.7 mmol) of glutaric anhydride. After stirring overnight (16 hours) at ambient temperature and for another 4 hours at 50° C., the solvent was removed in vacuo. The residue was chromatorgraphed to give 870 mg (66%) of a white solid.

NMR (DMSO-d$_6$): 0.1 (s, 6H, 2CH$_3$), 0.9 (s, 9H, 3CH$_3$), 1.6–2.5 (m, 10H, 3CH$_2$, H-2's, and H-3's), 3.72 (dd, J=2.4 and 11.6 Hz, 1H, H-5'a) 3.96 (dd, J=2.0 and 11.6 Hz, 1H, H-5'b), 4.1 (m, 1H, H-4'), 5.90 (dd, J=1.8 and 6.8 Hz, 1H, H-1'), 7.18 (d, J=8 Hz, 1H, H-5), 8.35 (d, 1H, H-6).

EXAMPLE 5

N,N'-(1,5-Pentanediyl)bis-[[2'3'-dideoxy-5'-0[(1,1-dimethylethyl)dimethylsilyl]cytidine To a solution of 1.1 g (2.5 mmol) of 5-N-[2'3'-Dideoxy-5'0-[(1,1-dimethylethyl)dimethylsilyl]-cytidinyl]-5-oxopentanoic acid (from Example 4) in 10 ml of dimethylformamide was added 1.14 g (5.5 mmol) of dicyclohexylcarbodiimide and 406 mg (3 mmol) of 1-hydroxybenzotriazole. After 0.5 hour at ambient temperature, 813 mg (2.5 mmol) 2'3'-dideoxy-5'-0[(1,1-dimethylethyl)dimethylsilyl]cytidine (from Example 1) was added and the mixture stirred overnight (16 hours) at ambient temperature. By following the work-up procedure described in Example 3, 344 mg (18%) of white solid was isolated after silica gel chromatography (5–15% MeOH in CH$_2$Cl$_2$).

NMR (CDCl$_3$): 0.16 (2s, 12H, 4CH$_3$), 0.96 (s, 18H, 6CH$_3$), 1.8–2.7 (m, 14H, 3CH$_2$, H-2's and H-3's), 3.72 (dd, J=2.4 and 11.6 Hz, 2H, H-5'a), 4.10 (dd, J=2.0 and 11.6 Hz, 2H, H-5'b), 4.20 (m, 2H, H-4'), 6.06 (dd, J=1.8 and 6.8 Hz, 2H, H-1'), 7.12 (d, J=8Hz, 2H, H-5), 8.52 (d, 2H, H-6).

EXAMPLE 6

2',3'-Dideoxy-5[[1-(2',3'-dideoxy-5'-0[(1,1-dimethylethyl)dimethylsilyl]pentofuranosyl]-1,2-dihydro-2-oxo-4-pyrimidinyl]amino]cytidine 5'-(5-oxopentanoate) (ester)

To a solution of 450 mg (1 mmol) of 5-N[2'3'-dideoxy-5'-0[(1,1-dimethylethyl)dimethylsilyl]-cytidinyl]-5-oxopentanoic acid (from Example 4) in 5 ml of dimethylformamide was added 200 mg (1.2 mmol) of carnbonyldiimidazole. After stirring at ambient temperature for 1 hour, 122 mg (1 mmol) of 2'3'-dideoxycytidine, followed by 34 mg (0.3 mmol) of potassium tert-butoxide was added. The mixture was stirred overnight (16 hours) at ambient temperature. After removal of solvent in vacuo, the residue was chromatographed (5–20% MeOH in CH$_2$Cl$_2$) to give 92 mg (14%) of a white solid.

NMR (CDCl$_3$) 0.1 (2s, 6H, 2 CH$_3$), 0.9 (s, 9H, 3 CH$_3$), 1.8–2.6 (m, 14H, H-2's, H-3's and 3 CH$_2$), 3.7–4.4 (m, 6H, H-4's and H-5's), 5.7 (d, J=8 Hz, 1H, H-5), 6.0 (m, 2H, H-1's), 7.3 (d, H=8 Hz, 1H, H-5), 7.8 (d, J=8 Hz, 1H, H-6), 8.6 (d, J=Hz, 1H, H-6).

EXAMPLE 7

2'3'-Dideoxy-5-[[1-[2',3'-dideoxy-5'-0[(1,1-dimethylethyl)dimethylsilyl]pentofuranosyl]-1,2-dihydro-2-oxo-4-pyrimidinyl]amino]adenosine 5'-(5-oxopentanoate) (ester)

By following the procedure and conditions described in Example 6, 160 mg (0.68 mmol) of 2',3'-dideoxyadenosine and 23 mg (0.2 mmol) of potassium tert-butoxide added to a reaction of 3.01 mg (0.68 mmol) of 5-N-[2',3'-dideoxy-5'[[1,1-dimethylethyl)dimethylsilyl)-cytidinyl]5-oxopentanoic acid (from Example 4) and 136 mg (0.82 mmol) of carbonyldiimidazole in 3.4 ml of dimethylforamide, followed by stirring for 17 hours, gave 65 mg (14%) of a white solid after silica gel chromatography (0–10% MeOH in CH$_2$Cl$_2$).

NMR (CDCl$_3$) 0.16 (2s, 6H, 2CH$_3$), 0.86 (S, 9H, 3CH$_3$), 1.8–2.7 (ml 4H, 3CH$_2$, H-2's and H3's), 3.7–4.7 (m, 6H, H-4's, and H-5's), 6.1 (dd, J=1.6 and 6.0 Hz 1H, H-1'), 6.33 (dd J=4.0 and 68 Hz, 1H, H-1'), 7.44 (d, J=8 Hz, 1H, H-5), 8.2 and 8.36 (2s, 2H, and H-8), 8.63 (d, J=8 Hz, 1H, H-6).

EXAMPLE 8

3'-Azido-3'-deoxy-4[[1-(2',3'-dideoxy-pentofuranosyl)-1,2-dihydro-2-oxo-4-pyrimidinyl]amino]-beta-D-erythro-thymidine-5'(4-oxobutanoate) (ester)

To a solution of 160 mg (0.24 mmol) of 3'-azido-3'-deoxy-4[[1-[2',3'-dideoxy-5'-0[(1,1-dimethylethyl)-dimethylsilyl]-pentofuranosyl]-1,2-dihydro-2oxo-4-pyrimidyl]amino]beta-D-erythro-thymidine-5'-(4-oxobutanoate) (ester) (from Example 3) in 2 ml of tetrahydrofuran was added 0.4 ml (0.4 mmol) of a 1M solution tetrabutylammonium fluoride in tetrahydrofuran. After stirring at ambient temperature for 2 hours, the solvent was removed in vacuo to afford a solid which was purified by preparative liquid chromatography (15% MeOH in CH$_2$Cl$_2$), to give 80 mg (61%) of the desired product as a white solid.

NMR (DMSO-d$_6$): 1.79 (s, 3H, CH$_3$), 1.8–2.8 (m, 1 OH, CH$_2$'s, H-2's and H-3's), 3.58 (dd, J=2.4 and 11.6 Hz, 1H, H-5'a), 3.76 (dd, J= and Hz, 1H, H-5'b), 3.98, 4.10, 4.28 and 4.46 (m, 5H total, H-3's, H-4's and H-5's), 5.10 (t, J=6 Hz, 1H, OH), 5.94 (dd, J=2.4 and 6.8 Hz, 1H, H-1'), 6.15 (t, J=6.4 Hz, 1H, H-1'), 7.17 (d, J=8 Hz, 1H, H-5), 7.50 (s, 1H, H-6), 8.50 (d, J=8 Hz, 1H, H-6), 10.93 and 11.36 (2bs, 2H, NH's).

EXAMPLE 9

3'-Azido-3'-deoxy-4[[1-(2',3'-dideoxy-pentofuranosyl)-1,2-dihydro-2-oxo-4-pyrimidinyl]amino]-beta-D-erythro-thymidine-5'-(4-oxo-butanoate) (ester)

A mixture of 346 mg (0.94 mmole) of 3'-Azido-3'-deoxy-beta-D-erythro-thymidine-5'-(hydrogenbutandioate) (from Example 2), 197 mg (0.94 mmol) of 2',3'-dideoxycytidine, 488 mg (2.37 mmoles) of dicyclohexylcarbodiimide, 315 mg (2.33 mmoles) of 1-hydroxybenzotriazole in 4 ml of pyridine was stirred overnight (16 hours) at ambient temperature. The solvent was removed in vacuo. Purification using preparative liquid chromatography (5–15% MeOH in $CH_2Cl_2$) gave 166 mg (32%) of a white solid.

EXAMPLE 10

N,N'-(1,5-dioxo-1,5-pentanediyl)bis(2',3'-dideoxycytidine)

By following the procedures and conditions described in Example 8, 1 ml (1 mmol) of a 1M solution tetrabutylammonium fluoride in tetrahydrofuran added to 340 mg (0.5 mmol) of N,N'-(1,5-dioxo-1,5-pentanediyl)bis[[2',3'-dideoxy-5'-0[(1,1-dimethylethyl)-dimethylsilyl]cytidine (from Example 5) in 2 ml of tetrahydrofuran, followed by stirring for 4 hours, gave 157 mg (66%) of a white solid after silica gel chromatography (10–20% MeOH in $CH_2Cl_2$).

NMR (DMSO-$d_6$): 1.7–2.5 (m, 7H, $Ch_2$ and H-2's and H-3's), 3.55 (dd, J=2.4 and 11.6 Hz, 1H, H-5'a), 3.75 (dd, J=2.0 and 11.6 Hz, 1H, H-5'b), 4.08 (m, 1H, H-4'), 5.1 (t, J=5.2 Hz, 1H, OH), 5.90 (dd, J=1.8 and 6.8 Hz, 1H, H-1'), 7.17 (d, J=8 Hz, 1H, H-5), 8.45 (d, J=8 Hz, 1H, H-6).

EXAMPLE 11

2',3'-Dideoxy-5-[[1-(2',3'-dideoxypentofuranosyl)-1,2-dihydro-2-oxo-4-pyrimidinyl]amino]cytidine-5'-(5-oxopentanoate) (ester)

By following the procedures and conditions described in Example 8, 0.1 ml (0.1 mmol) of a 1M solution tetrabutylammonium fluoride in tetrahydrofuran added to 92 mg of 2',3'-dideoxy-5-[[1-[2',3'-dideoxy-5'-0[(1,1-dimethylethyl)dimethylsilyl]pentofuranosyl]1,2-dihydro-2-oxo-4-pyrimidinyl]amino]cytidine 5'-(5-oxopentanoate) (ester) (from Example 6) in 0.5 ml of tetrahydrofuran, followed by stirring for 3 hours, gave 28 mg (36%) of a white solid after reverse-phase silica gel high performance liquid chromatography (20% $CH_3CN$ in $H_2O$).

NMR ($CDCl_3$+$CH_3OD$): 1.8–2.6 (m, 14H, 3$CH_2$, H-2's and H-3's), 3.7 (dd, J=3.8 and 12 Hz; 1H, H-5'), 4.0 (dd, J=2 and 12 Hz, 1H, H-5) 4.1–4.5 (m, 4H, 2H-4' and H-5's), 5.77 (d, J=8 Hz, 1H, H-5), 5.92 (dd, J=2.4 and 6.8 Hz, 1H, H-1'), 6.0 (dd, J=1.8 and 6.8 Hz, 1H, H-1'), 7.33 (d, 1H, J=8Hz, H-5), 7.78 (d, J=8Hz, 1H, H-6), 8.52 (d, J=8 Hz, 1H, H-6).

EXAMPLE 12

2',3'-Dideoxy-5[[1-(2',3'-dideoxypentofuranosyl)-1,2-dihydro-2-oxo-4-pyrimidinyl]amino]adenosine-5'-(5-oxopentanoate) (ester)

By following the procedures and conditions described in Example 8, 0.15 ml (0.15 mmol) of a 1M solution of tetrabutylammonium fluoride in tetrahydrofuran added to 65 mg (0.099 mmol) of 2',3'-dideoxy-5[[1-[2',3'-dideoxy-5'-0-[(1,1-dimethylethyl)dimethylsilyl)pentofuranosyl-1,2-dihydro-2-oxo-4-pyrimidinyl)-amino]adenosine 5'-(5-oxopentanoate) (ester) (from Example 7) in 1 ml of tetrahydrofuran, followed by stirring for 1.5 hours, gave 20 mg (37%) of a white solid after silica gel chromatography (4–12% MeOH in $CH_2Cl_2$).

NMR ($CDCl_3$+$CD_3OD$) 1.95–2.7 (m, 14H, 3 $CH_2$, H-2's and H-3's), 3.7–4.7 (m, 6H, H-4's and H-5's), 6.2 (dd, J=1.8 and 6.8 Hz, 1H, H-1'), 6.30 (dd, J=4.0 and 6.8 Hz, 1H, H-1'), 7.35 (d, J=8 Hz, 1H, H-5), 8.19 and 8.32 (2s, 2H, H-2 and H-8), 8.40 (d, J=8 Hz, 1H, H-6)

EXAMPLE 13

2',3'-Dideoxy-N-[(dimethylamino)methylene]cytidine

To a solution of 1.05 g (5 mmol) of 2',3'-dideoxycytidine in 5 ml of dimethylforamide was added 2 ml (15 mmol) of N,N-dimethylforamide dimethylacetal. After stirring at ambient temperature for 15 hours, the reaction solution was evaporated in vacuo to give 1.2 (93%) of a pale yellow solid.

NMR ($CDCl_3$): 1.8–2.6 (m, 4H, H-2's and H-3's), 3.76 (dd, J=4 and 12 Hz, 1H, H-5'a), 4.02 (dd, J=3 and 12 Hz, 1H, H-5'b), 4.24 (m, 1H, H-4'), 6.07 (d, J=8 Hz, H-5), 6.12 (dd, J=4 and 7 Hz, 1H, H-1'), 7.98 (d, J=8 Hz, 1H, H-6), 8.84 (s, 1H, =CH).

EXAMPLE 14

2',3'-Dideoxycytidine 5',5''-carbonate

To a solution of 380 mg (1.4 mmol) of 2',3'-dideoxy N-[(dimethylamino)methylene)cytidine (from Example 13) in 4 ml of dimethylforamide was added 146 mg (1.09 mmol) of carbonyldimiidazole, followed by 23 mg (0.2 mmol) of potassium tert-butoxide. The mixture was stirred for 2 hours at ambient temperature. After removal of solvent in vacuo, the residue was dissolved in 5 ml of methanol containing 40 mg (0.2 mmol) of p-toluenesulfonic acid monohydrate. The mixture was stirred for 7 hours at ambient temperature. After removal of solvent in vacuo, the residue was chromatographed (20% MeOH in $CH_2Cl_2$) to give 106 mg (34%) of a white solid.

NMR (DMSO-$d_6$): 1.65–2.35 (m, 8H, H-2's and H-3's), 4.15–4.35 (m, 6H, H-4's and H-5's), 5.65 (d, J=8 Hz, 2H, 2H-5), 6.00 (dd, J=3.2 and 6.8 Hz, 2H, 2H-1'), 7.1 (m, 4H, 2 $NH_2$), 7.6 (d, J=8 Hz, 2H, 2H-6).

We claim:

1. A compound of formula

wherein A and C are each independently dideoxynucleoside radicals and B is a linking group represented by the formula

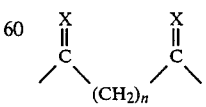 (a)

 (b)

-continued

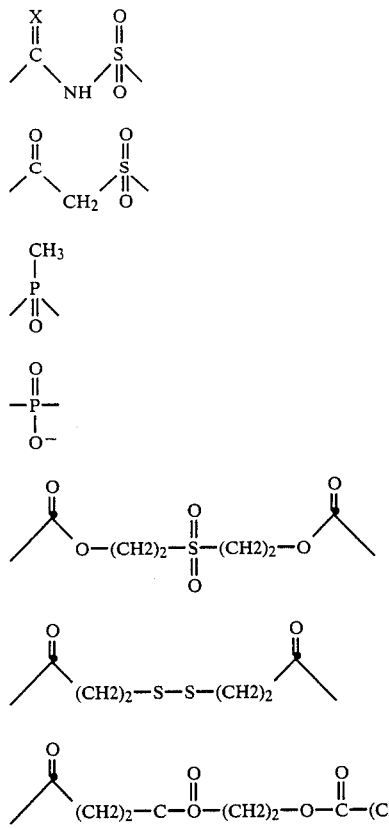

with X=O or S and n=2-6 and B is attached to A at the 4 amino or the 5' hydroxy position of A; and C is attached to B at the 4 amino or 5' hydroxy position of C.

2. A compound of the formula

A—B—C wherein A and C are each independently dideoxynucleoside radicals and B is a linking group represented by the formula (a) 

(b)

(c)

(d)

(e)

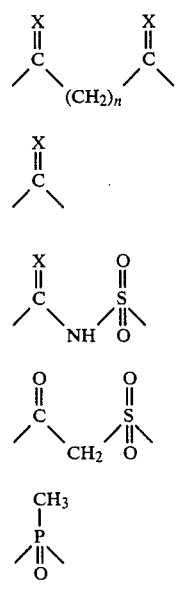

-continued (f)

(g)

(h)

(i)

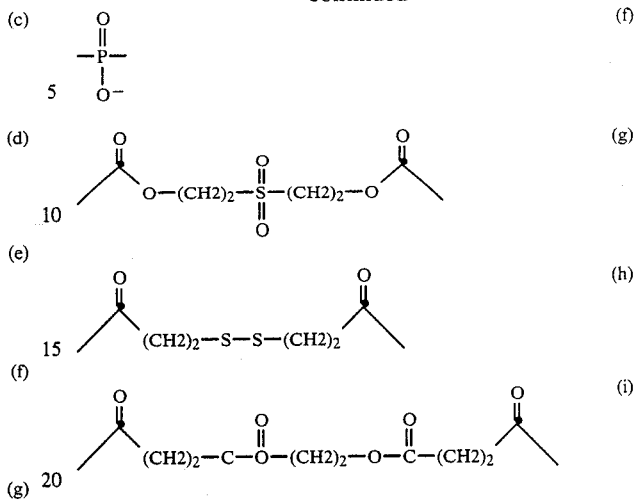

with X=O or S and n=2-6; and B is attached to A at the amino position of A and C is attached to B at the 5' hydroxy position of C.

3. The compound of claim 2 wherein A or C is selected from the group consisting of dideoxycytidine, dideoxyadenosine or 3'-azido-3'-deoxythymidine.

4. The compound of claim 3 wherein A is dideoxycytidine.

5. The compound of claim 4 wherein B is

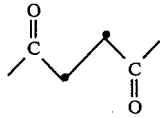

and C is 3'-azido-3'-deoxythymidine said compound having the formula

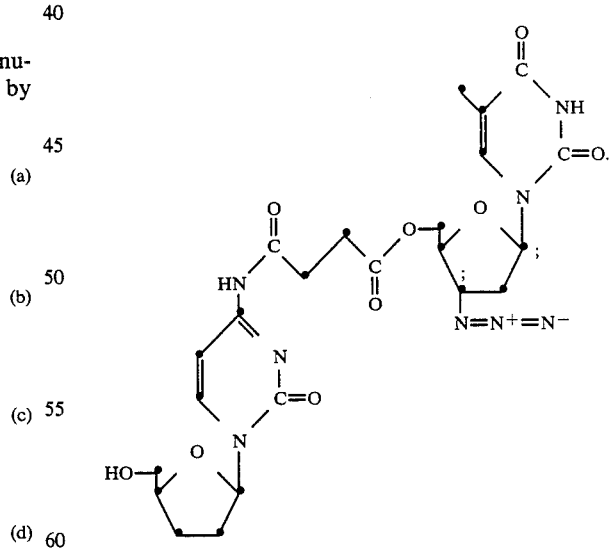

6. The compound of claim 4 wherein B is

and C is dideoxycytidine said compound having the formula

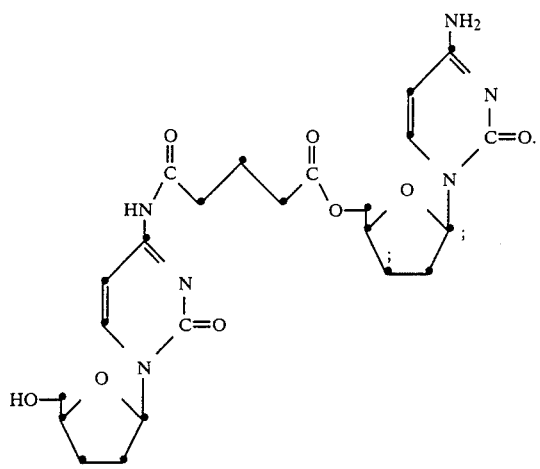

7. The compound of claim 4 wherein B is

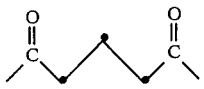

and C is dideoxyadenosine said compound having the formula

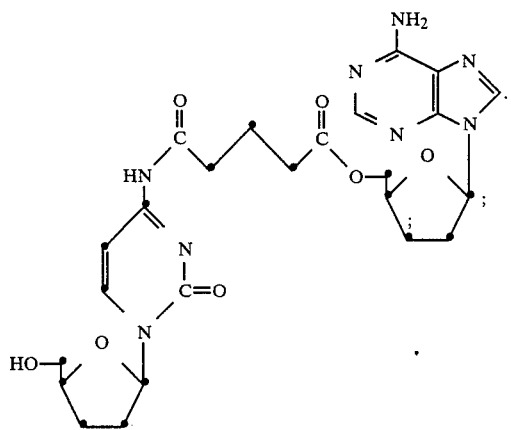

8. A compound of the formula

wherein A and C are each independently dideoxynucleoside radicals and B is a linking group represented by the formula

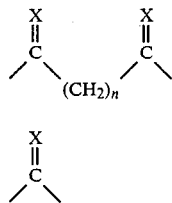

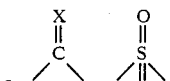 (c)

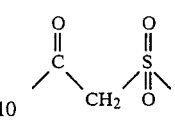 (d)

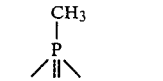 (e)

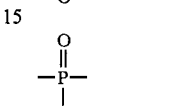 (f)

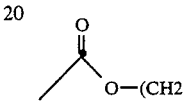 (g)

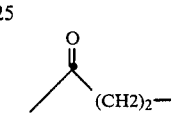 (h)

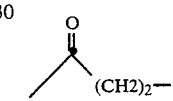 (i)

with X=O or S and n=2-6 and B is attached to A at the 5' hydroxy position of A and C is attached to B at the 5' hydroxy position of C.

9. The compound of claim 8 wherein A or C is selected from the group consisting of dideoxycytidine, dideoxyadenosine or 3'-azido-3'-deoxythymidine.

10. The compound of claim 9 wherein A is dideoxycytidine.

11. The compound of claim 10 whereiin B is

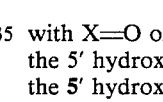

and C is 3'azido-3'-deoxythymidine said compound having the formula

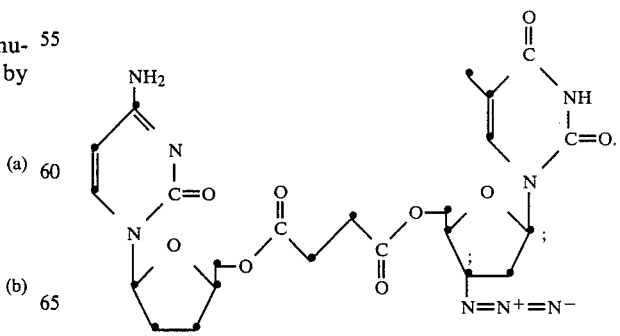

12. The compound of claim 10 wherein B is

and C is dideoxycytidine said compound having the formula

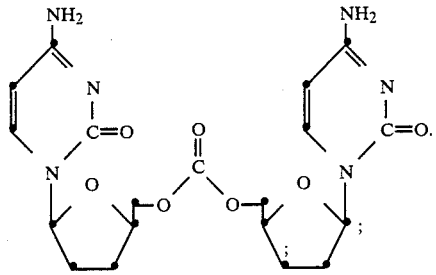

13. The compound of claim 10 wherein B is

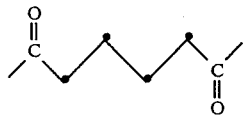

and C is dideoxycytidine said compound having the formula

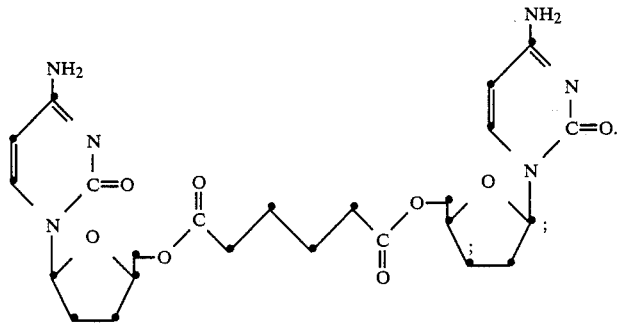

14. A compound of the formula

A—B—C wherein A and C are dideoxynucleoside radicals and B is a linking group represented by the formula

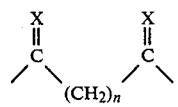 (a)

 (b)

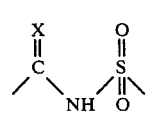 (c)

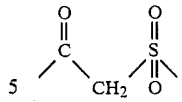 (d)

 (e)

 (f)

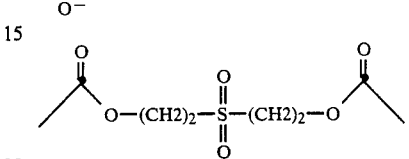 (g)

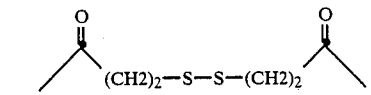 (h)

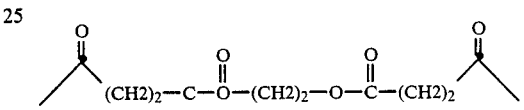 (i)

with X=O or S and n=2–6 and B is attached to A at the 4-amino position of A and C is attached to B at the 4-amino position of C.

15. The compound of claim 14 wherein A or C is selected from the group consisting of dideoxycytidine, dideoxyadenosine, or 3′-azido-3′-dieoxythymidine.

16. The compound of claim 15 wherein A is didoxycytidine.

17. The compound of claim 16 wherein B is

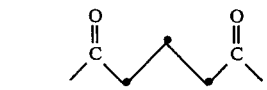

and C is dideoxycytidine said compound having the formula

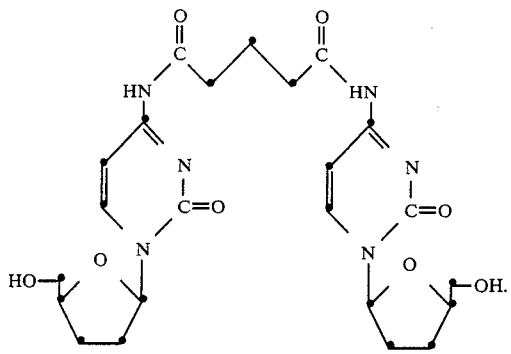

18. A method of preventing a retroviral infection in a subject comprising administering to the subject a virus inactivating effective amount of a compound of the formula

A—B—C wherein A and C are each independently dideoxynucleoside radicals; and B is a linking group represented by the formula

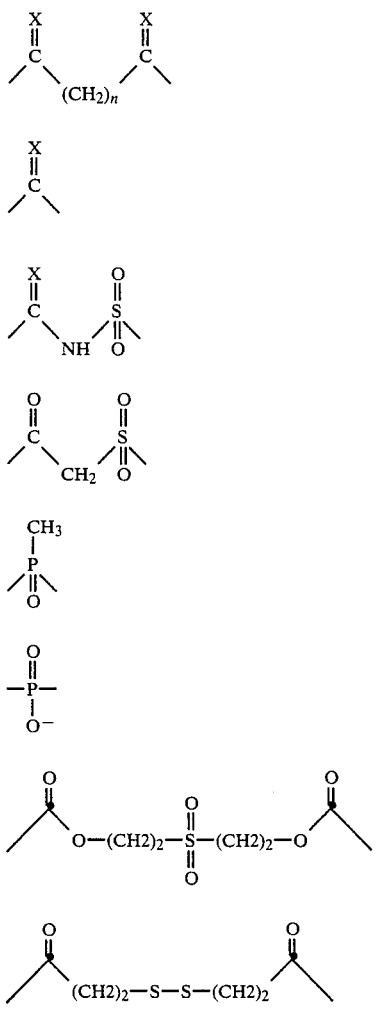

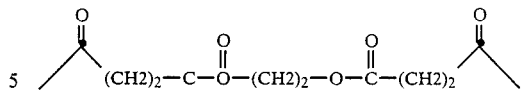

with X=O or S and n=2-6; and B is attached to A at the 4 amino or the 5' hydroxy position of A; and C is attached to B at the 4 amino or the 5' hydroxy position of C.

19. The method of claim 18 wherein the retrovirus is the HIV virus.

20. The method of claim 18 wherein the compound is administered orally.

21. The method of claim 18 wherein the compound is administered intravenously.

22. A method of treating a subject infected with a retrovirus comprising administering to the subject a virus inactivating effective amount of a compound of the formula:

(a) A—B—C wherein A or C each independently is a dideoxynucleoside radical; and B is a linking group represented by the formula

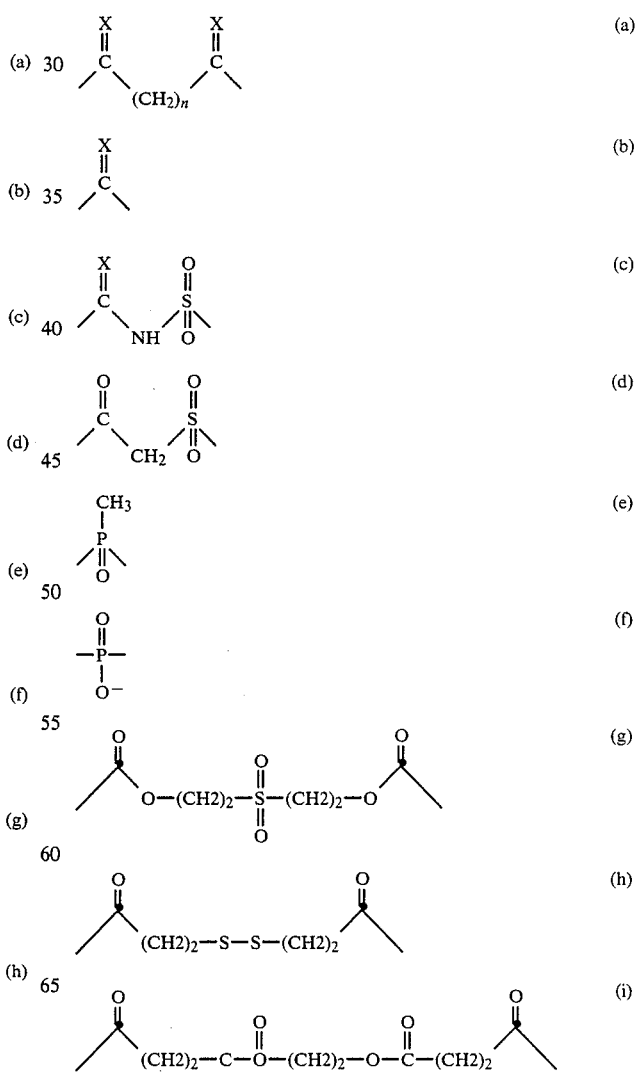

with X=O or S and n=2-6; and B is attached to A at either the 5' hydroxy position at the 4 amino position of A; and C is attached to B at either the 5' hydroxy positon or the amino position of C; or the pharmaceutically acceptable salts.

23. The method of claim 22 wherein the retrovirus is the HIV virus.

24. The method of claim 22 wherein the compound is administered orally.

25. The method of claim 22 wherein the compound is administered intravenously.

26. A compound of the formula A or C wherein A or C is a dideoxynucleoside and either the 5' hydroxy position or the amino position of A or C is blocked with a conventional hydroxyl or amine blocking group known in the art.

27. The compound of claim 26 wherein the hydroxyl blocking group is tertbutyldimethyl chlorosilyl.

28. The compound of claim 26 wherein the amine blocking groups is dimethylaminomethylene.

29. The compound of claim 26 wherein A or C is dideoxycytidine said compound having the formula

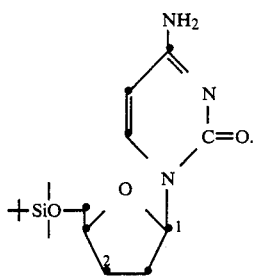

30. The compound of claim 26 wherein A or C is dideoxycytidine and of the formula

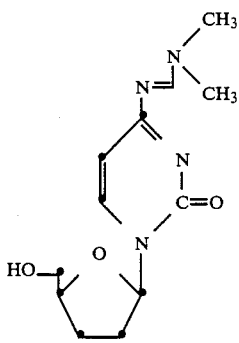

31. A compound of the formula A—B or B—C wherein A and C are each independently dideoxynucleoside radicals and B is a linking group represented by the formula

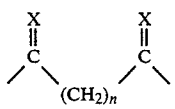 (a)

 (b)

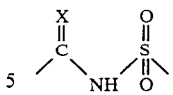 (c)

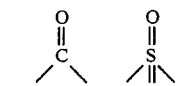 (d)

 (e)

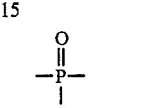 (f)

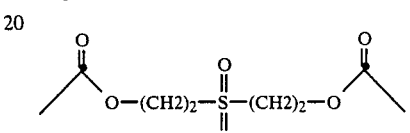 (g)

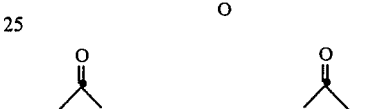 (h)

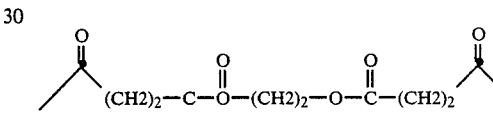 (i)

with x=O or S and n=2-6 and B is attached to A or C at either the 5' hydroxy position of the 4 amino position of A or C.

32. The compound of claim 31 wherein A or C each independently is 3'-azido-3'-deoxythymidine and B is

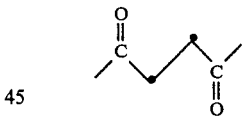

and B is attached to A or C at the 5' hydroxy position of A or C said compound having the formula

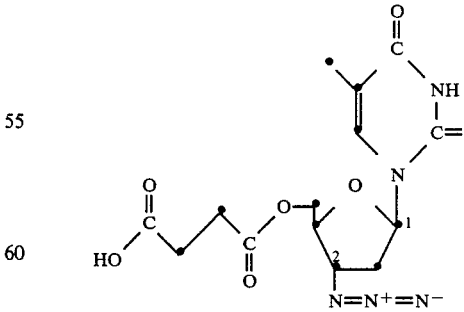

33. The compound of claim 31 wherein the 5' hydroxy position or the amino position of A or C which is not linked to B is blocked with one or more conventional hydroxyl or amine blocking groups known in the art.

34. The compound of claim 31 wherein the hydroxyl blocking group is tertbutyldimethylchlorosilyl and the amine blocking group is dimethylaminomethylene.

35. The compound of claim 31 wherein B is

and the 5' hydroxy position of A is blocked; said compound having the formula

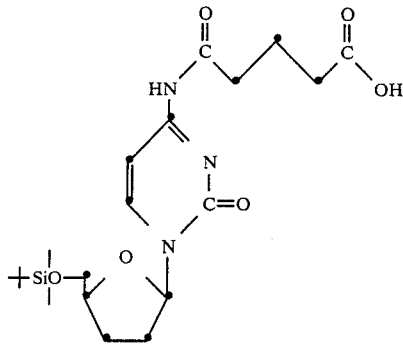

36. A compound of the formula

A—B—C wherein A or C are each independently dideoxynucleoside radicals and B is a linking group represented by the formula

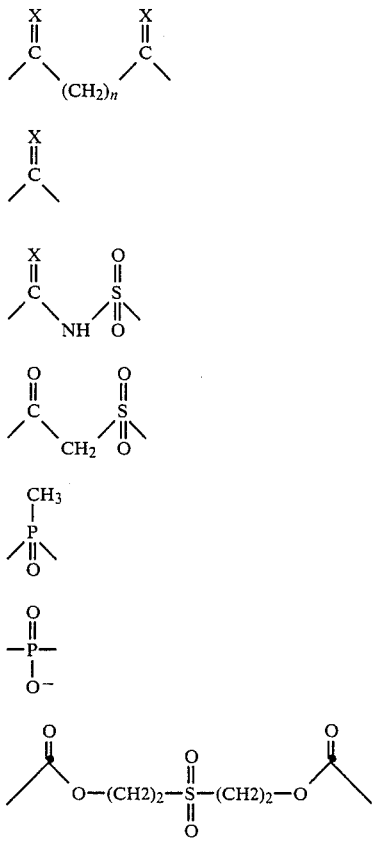

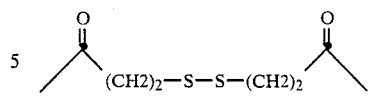

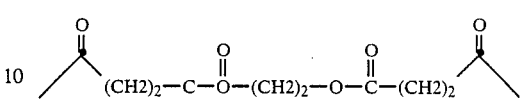

with X—O or S and n=2–6; and B is attached to A at the amino position of A and C is attached to B at the 5' hydroxy position of C and one or more of the remaining 5' hydroxy positions or amino positions of A or C which is not linked to B are blocked with conventional hydroxyl or amine blocking groups known in the art.

37. The compound of claim 36 wherein the hydroxyl blocking group is tertbutyldimethylchlorosilyl and the amine blocking group is dimethylaminomethylene.

38. The compound of claim 36 wherein A is dideoxycytidine, B is

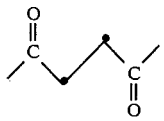

and C is 3'-azido-3'-deoxythymidine and the 5' hydroxy position of A is blocked; said compound having the formula

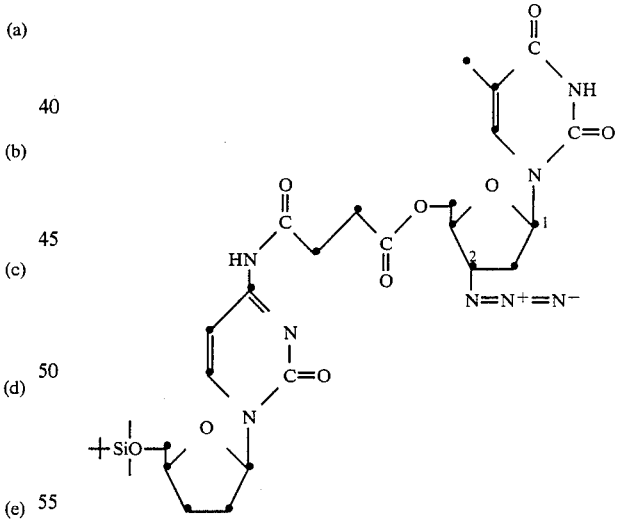

39. The compound of claim 36 wherein A and C are dideoxycytidine and B is

and B is attached to A and C at the amino positions of A and C and the 5' hydroxy positions of A and C are blocked; said compound having the formula:

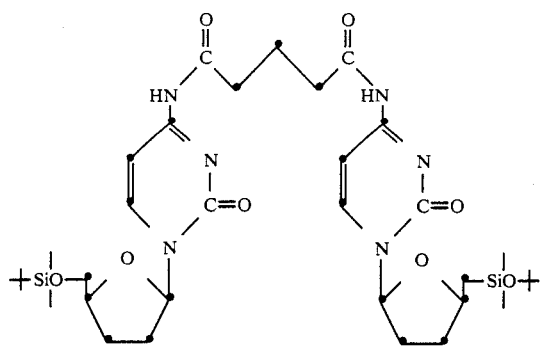

40. The compound of claim 36 wherein A is dideoxycytidine and C is dideoxyadenosine and B is

and B is attached to A at the 4 amino position of A and C is attached to B at the 5' hydroxy position of C and the 5' hydroxy position of A is blocked; said compound having the formula

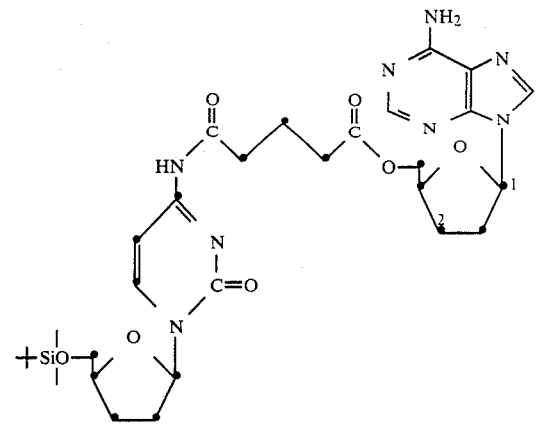

41. The compound of claim 36 wherein A and C are dideoxycytidine and B is

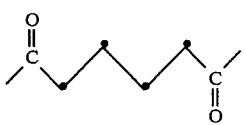

and B is attached to A and C at the 5' hydroxy positions of A or C and the amino positions of A or C are blocked; said compound having the formula

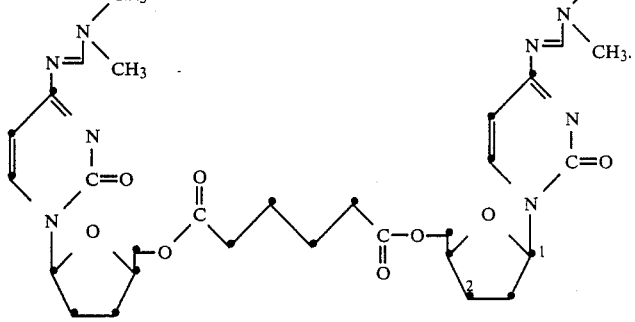

* * * * *